(12) United States Patent
Sheth et al.

(10) Patent No.: US 11,020,059 B2
(45) Date of Patent: Jun. 1, 2021

(54) SYSTEM AND METHOD FOR DIAGNOSING AND NOTIFICATION REGARDING THE ONSET OF A STROKE

(71) Applicant: YALE UNIVERSITY, New Haven, CT (US)

(72) Inventors: Kevin N. Sheth, Madison, CT (US); Hitten P. Zaveri, New Haven, CT (US); Ronald R. Coifman, North Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 244 days.

(21) Appl. No.: 16/069,548

(22) PCT Filed: Jan. 12, 2017

(86) PCT No.: PCT/US2017/013149
§ 371 (c)(1),
(2) Date: Jul. 12, 2018

(87) PCT Pub. No.: WO2017/123725
PCT Pub. Date: Jul. 20, 2017

(65) Prior Publication Data
US 2019/0029606 A1 Jan. 31, 2019

Related U.S. Application Data
(60) Provisional application No. 62/277,645, filed on Jan. 12, 2016.

(51) Int. Cl.
*A61B 5/00* (2006.01)
*A61B 5/11* (2006.01)
(Continued)

(52) U.S. Cl.
CPC .......... *A61B 5/7282* (2013.01); *A61B 5/0022* (2013.01); *A61B 5/1114* (2013.01);
(Continued)

(58) Field of Classification Search
CPC ... A61B 5/7282; A61B 5/6829; A61B 5/7275; A61B 5/0022; A61B 5/1114;
(Continued)

(56) References Cited

U.S. PATENT DOCUMENTS

2008/0294019 A1 11/2008 Tran
2009/0149913 A1 6/2009 Putz et al.
(Continued)

OTHER PUBLICATIONS

Jose R. Villar et al: "A hybrid intelligent recognition system for the early detection of strokes", Integrated Computer-Aided Engineering, val. 22, No. 3, Jun. 2, 2015 (Jun. 2, 2015), pp. 215-227, XP055589561, NL; ISSN: 1069-2509, DOI: 10.3233/ICA-150488.
(Continued)

*Primary Examiner* — Eric F Winakur
*Assistant Examiner* — Abid A Mustansir
(74) *Attorney, Agent, or Firm* — Welsh Flaxman & Gitler LLC

(57) ABSTRACT

A real-time automated method to diagnose and/or detect stroke and engage the patient, care-takers, emergency medical system and stroke neurologists in the management of this condition includes the steps of continuously measuring natural limb activity, conveying the measurements to a cloud based real-time data processing system, identifying patient specific alert conditions, and determining solutions for acting upon needs of the patient. The system by which the method is implemented includes at least one body worn sensor continuously measuring natural limb activity and a patient worn data transmission device conveying the measurements to a cloud based real-time data processing system (Continued)

that identifies patient specific alert conditions and determines solutions for acting upon needs of the patient.

25 Claims, 9 Drawing Sheets

(51) Int. Cl.
*G16H 10/60* (2018.01)
*A61B 5/0205* (2006.01)
*A61B 5/024* (2006.01)
*A61B 5/0533* (2021.01)

(52) U.S. Cl.
CPC .......... *A61B 5/1118* (2013.01); *A61B 5/6824* (2013.01); *A61B 5/6828* (2013.01); *A61B 5/6829* (2013.01); *A61B 5/7275* (2013.01); *A61B 5/746* (2013.01); *G16H 10/60* (2018.01); *A61B 5/02055* (2013.01); *A61B 5/02438* (2013.01); *A61B 5/0533* (2013.01); *A61B 5/1122* (2013.01); *A61B 5/4064* (2013.01); *A61B 2505/01* (2013.01); *A61B 2505/09* (2013.01); *A61B 2562/0219* (2013.01)

(58) Field of Classification Search
CPC ..... A61B 5/6828; A61B 5/746; A61B 5/1118; A61B 5/6824; A61B 2505/01; A61B 5/1122; A61B 5/02055; A61B 5/02438; A61B 5/0533; A61B 5/4064; A61B 2505/09; A61B 2562/0219; G16H 10/60; G16H 40/67; G16H 50/30
See application file for complete search history.

(56) References Cited

U.S. PATENT DOCUMENTS

| | | |
|---|---|---|
| 2009/0204030 A1 | 8/2009 | Brauers et al. |
| 2009/0264785 A1 | 10/2009 | Causevic et al. |
| 2014/0243637 A1 | 8/2014 | Rahman et al. |
| 2015/0157252 A1* | 6/2015 | Sabesan ............... A61B 5/7246 600/301 |

OTHER PUBLICATIONS

Lafon et al: Data Fusion and Multicue Data Matching by Diffusion Maps:, IEEE Transactions on Pattern Analysis and Machine Intelligence, IEEE Computer Society, USA, vol. 27. No. 11, Nov. 1, 2006 (Nov. 1, 2006). pp. 1784-1797. XP011149295, ISSN: 0162-8828. DOI: 10.1109/TPAMI.2006.223.

* cited by examiner

A comparison of Runner 3 (speed 7.5) and Runner 11 (speed 7.5). The profile for each runner is shown in a different line type. The difference between the two profiles, d = 1.0548. This indicates that the two runners can be easily distinguished based on the profile.

A comparison of Runner 10 (speed 7.5) in two different trials. The difference between the two profiles, d = 0.0599. This indicates that two profiles are strongly overlapped and nearly identical.

Match Rank Frequencies. Pairwise runner comparison for all the trials. Most pairwise comparisons return a match rank of 1. That is each trial from a runner is being matched to another trial from the same runner.

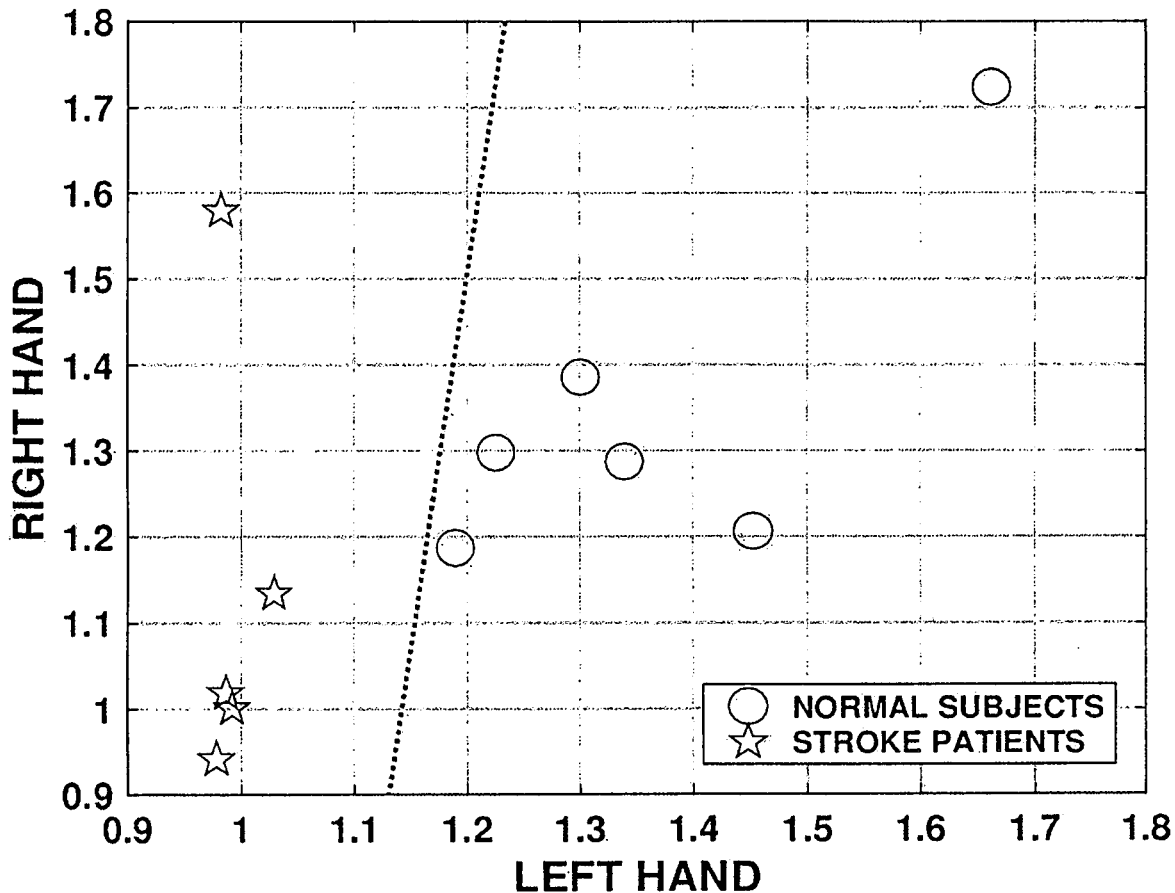

FIG. 10

The average absolute acceleration measured from the left and right hand of stroke patients (n= 5; shown with a star symbol) and normal subjects (n= 6; shown as a circle) measured while the individuals performed the following simple task: "cross your arms over each other five times". The acceleration values measured from each hand were averaged over the X, Y and Z axis. The results for the right hand are plotted as the ordinate (Y axis), and the results for the left hand are plotted as the abscissa (X axis). A linear classifier boundary is shown as a dashed line. A perfect classification results from the classification boundary. That is, there is complete separation between stroke patients and normal subjects.

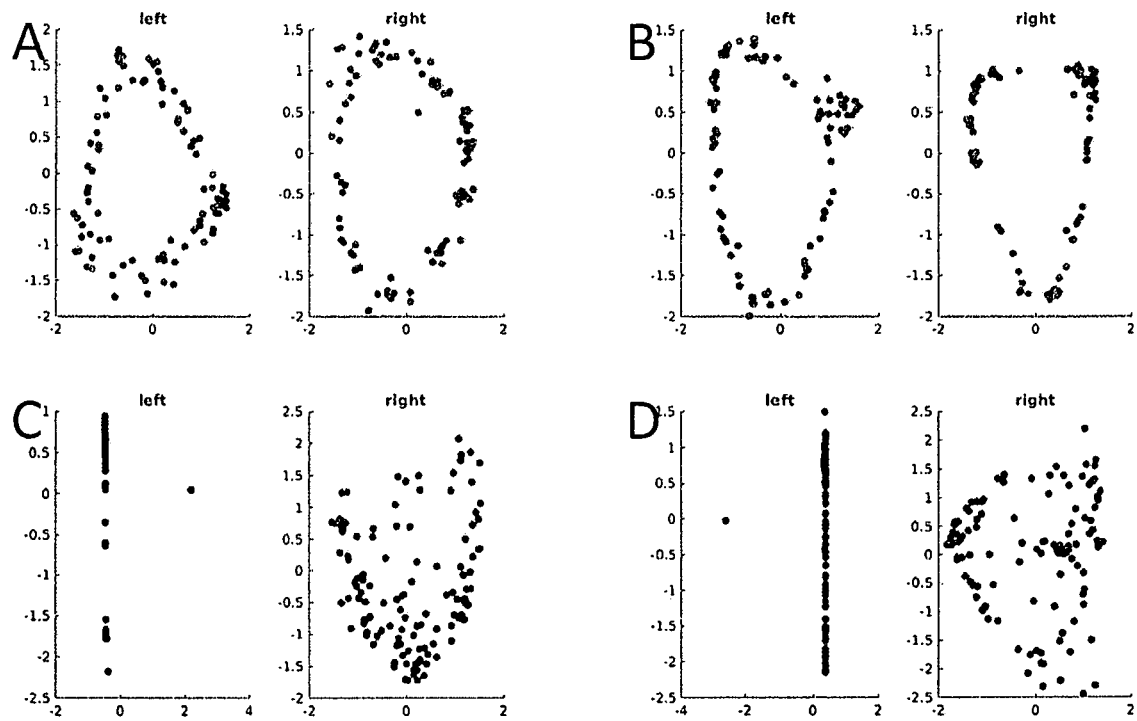

FIG. 11

Example diffusion maps calculated from acceleration values measured from two normal subjects (a,b), and two stroke patients (c,d) while the individuals were performing the following task: "cycle your fists in front of you". Here, the diffusion maps are shown separately for each hand. Note, the diffusion maps for the normal subjects capture the circular trajectory of the motion of each hand. For the patients however, the diffusion maps indicate the absence of circular motion for the left hand (the side of the weakness), and a distorted trajectory for the right hand. The hand dynamics for the normal subjects and the stroke patients are very different and this difference is clearly captured by the diffusion maps.

SYSTEM AND METHOD FOR DIAGNOSING AND NOTIFICATION REGARDING THE ONSET OF A STROKE

CROSS REFERENCE TO RELATED APPLICATION

This application claims the benefit of U.S. Provisional Patent Application Ser. No. 62/277,645, entitled "SYSTEM AND METHOD FOR DIAGNOSING AND NOTIFICATION REGARDING THE ONSET OF A STROKE," filed Jan. 12, 2016.

BACKGROUND OF THE INVENTION

1. Field of the Invention

The invention relates to a system and method for diagnosis, detection and notification regarding the onset of a stroke.

2. Description of the Related Art

Ischemic stroke is the fifth leading cause of death, and a leading cause of disability in the United States, affecting 700,000 Americans every year. Even though intravenous (IV) tissue plasminogen activator (tPA) has been an FDA approved therapy since 1995, twenty years later, less than 10% of eligible patients receive this therapy.

IV tPA is a treatment for acute ischemic stroke with proven benefit. tPA is a protein involved in the breakdown of blood clots. It is a serine protease found on endothelial cells, the cells that line the blood vessels. As an enzyme, it catalyzes the conversion of plasminogen to plasmin, the major enzyme responsible for clot breakdown. As a result of its work on the clotting system, tPA is effectively used to treat strokes. Even though it is the only approved therapy for stroke, rates of tPA administration to all ischemic stroke patients are exceedingly low. In addition, there is robust population level data to show that every minute of delay results in worse outcome.

Treatment with tPA in a 3-4.5 hour time-window after the onset of a stroke can increase favorable outcome, although this indication has not been approved by the FDA. Overall, only 22% of all stroke patients in the U.S. arrive within the first several hours of stroke onset, and recent epidemiological studies indicate that approximately 7% are treated with IV tPA. Mechanical thrombolysis may be effective in a subset of these early presenting patients, particularly in those whom IV tPA is not effective. Subsequent management is largely supportive, with a focus on identifying the etiology to prevent stroke recurrence. Because pain is usually absent from symptoms of stroke and because patients are neurologically disabled, patients routinely face a delay in timely diagnosis. Which in turn affects both their potential eligibility for these acute therapies and when received, the potential efficacy they may derive from its administration.

Two strategies have been employed to date in order to reach patients faster. First is the "drip and ship" strategy where patients arrive at community hospitals, are connected to stroke neurologists through telemedicine and then transferred while tPA is being administered. The second, more recent approach is to place a CT (computed tomography) scanner in an ambulance to bring the emergency room to the patient. Both of these approaches are inefficient, expensive, and have not made a significant impact in tPA administration rates.

Despite massive public health campaigns, identifying symptoms of stroke and activating emergency response systems within the 4.5 hour time window for effective IV tPA treatment continues to remain a major challenge. The solution, real time detection of stroke, remains a major public health goal with financial consequences of billions of dollars and a reduction in disability or death for tens of thousands of patients.

The present invention seeks to solve this major gap in clinical practice, which is real-time diagnosis and/or detection of ischemic and hemorrhagic stroke and acute central nervous system injury. The development of a real-time automated system and method to diagnose stroke and to engage the emergency medical system and stroke neurologists has the potential to dramatically shorten the time to definitive therapy for patients with stroke.

SUMMARY OF THE INVENTION

It is, therefore, an object of the present invention to provide a real-time automated method to diagnose and/or detect stroke and engage the patient, care-takers, emergency medical system and stroke neurologists in the management of this condition. The method includes the steps of continuously measuring natural limb activity, conveying the measurements to a cloud based real-time data processing system, identifying patient specific alert conditions, and determining solutions for acting upon needs of the patient.

It is also an object of the present invention to provide a method wherein the step of determining solutions includes providing for notification of potential stroke syndromes in real-time and activating acute stroke protocols.

It is another object of the present invention to provide a method wherein the step of identifying includes establishing patient specific limb activity signature through the aggregation of continuously sampled data acquired over days, weeks and months.

It is a further object of the present invention to provide a method wherein the step of continuously measuring natural limb activity includes positioning four body worn sensors on the limbs of the patient.

It is also an object of the present invention to provide a method wherein the step of conveying the measurements includes adding a time-stamp to a data stream generated by continuously monitoring limb activity.

It is another object of the present invention to provide a method wherein the step of determining solutions includes identifying treatment protocols.

It is a further object of the present invention to provide a method wherein the treatment protocols include activation of the emergency medical response system, transport of the patient to the nearest Neurocritical Care Unit or emergency room for rapid evaluation and treatment.

It is also an object of the present invention to provide a method wherein the step of identifying patient specific alert conditions includes creating diffusion maps representative of the patient's limb movement.

It is another object of the present invention to provide a method for determining whether the current limb movements of the patient are within expected parameters, in comparison to a previously determined patient specific limb activity signature, wherein the step of identifying patient specific alert conditions includes continuously processing limb activity and sensor data.

It is a further object of the present invention to provide a method including the step of quantifying the resulting magnitude of the deficit.

It is also an object of the present invention to provide a method including the step of quantify the degree of success in restoring function during rehabilitation.

It is a further object of the present invention to provide a real-time automated system to diagnose and/or detect stroke and engage the patient, care-takers, emergency medical system and stroke neurologists in the management of this condition. The system includes at least one body worn sensor continuously measuring natural limb activity and a patient worn data transmission device conveying the measurements to a cloud based real-time data processing system that identifies patient specific alert conditions and determines solutions for acting upon needs of the patient.

It is also an object of the present invention to provide a system wherein the data processing system establishes a patient specific limb activity signature through the aggregation of continuously sampled data acquired over days, weeks and months.

It is another object of the present invention to provide a system including four body worn sensors shaped and dimensioned to be worn on limbs of the patient.

It is a further object of the present invention to provide a system wherein the patient worn data transmission device adds a time-stamp to a data stream generated by at least one body worn sensor.

It is also an object of the present invention to provide a system wherein the data processing system adds a time-stamp to data conveyed by the patient worn data transmission device.

It is another object of the present invention to provide a system wherein at least one body worn sensor includes a motion tracking device.

It is a further object of the present invention to provide a system wherein the data processing system identifies treatment protocols.

It is also an object of the present invention to provide a system wherein the treatment protocols includes activation of the emergency medical response system, transport of the patient to the nearest Neurocritical Care Unit or emergency room for rapid evaluation and treatment.

It is another object of the present invention to provide a system method wherein the data processing system includes an acquisition system, an analysis system, and a patient management system.

It is a further object of the present invention to provide a system wherein the analysis system creates diffusion maps representative of the patient's limb movement.

It is also an object of the present invention to provide a system wherein the analysis system continuously processes limb activity and sensor data, and determines, in comparison to a previously determined patient specific limb activity signature if the current limb movements of the patient are within expected parameters.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 10 is a graph showing the average absolute acceleration measured from the left and right hand of stroke patients (n=5; shown with a star symbol) and normal subjects (n=6; shown as a circle) measured while the individuals performed the following simple task: "cross your arms over each other five times". The acceleration values measured from each hand were averaged over the X, Y and Z axis. The results for the right hand are plotted as the ordinate (Y axis), and the results for the left hand are plotted as the abscissa (X axis). A linear classifier boundary is shown as a dashed line. A perfect classification results from the classification boundary. That is, there is complete separation between stroke patients and normal subjects.

FIG. 11 shows exemplary diffusion maps calculated from acceleration values measured from two normal subjects (a,b), and two stroke patients (c,d) while the individuals were performing the following task: "cycle your fists in front of you". The diffusion maps are shown separately for each hand. Note, the diffusion maps for the normal subjects capture the circular trajectory of the motion of each hand. For the patients however, the diffusion maps indicate the absence of circular motion for the left hand (the side of the weakness), and a distorted trajectory for the right hand. The hand dynamics for the normal subjects and the stroke patients are very different and this difference is clearly captured by the diffusion maps.

DESCRIPTION OF THE PREFERRED EMBODIMENTS

Figure 1:
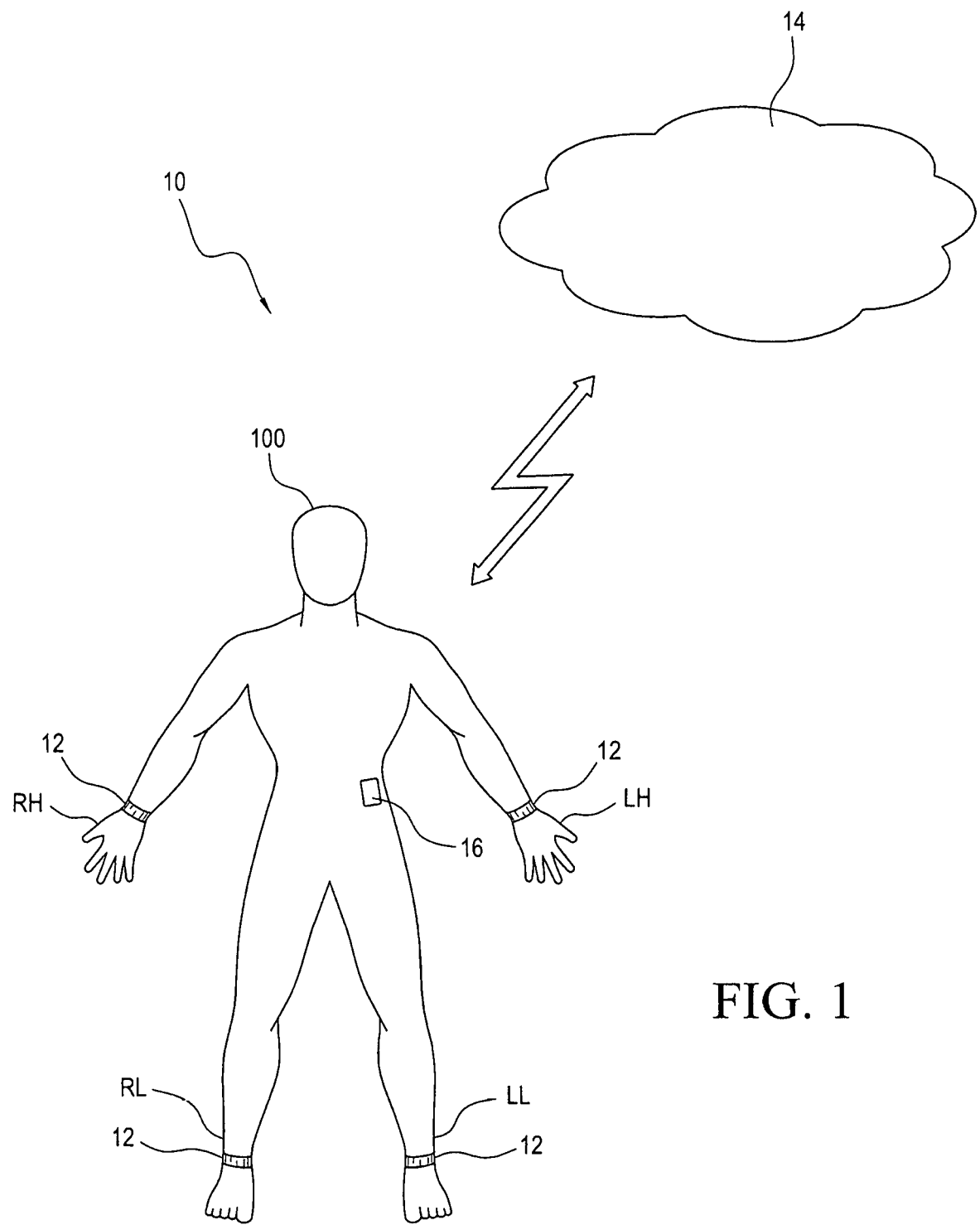
FIGS. 1 and 2 are schematics of the present system and method for detection and notification regarding the onset of a stroke.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to the various figures, the present invention provides a real-time automated system and method to diagnose and/or detect stroke and engage the patient, care-takers, emergency medical system and stroke neurologists in the management of this condition. The present system and method for diagnosis, detection and notification regarding the onset of a stroke (hereinafter "system 10"), employs body worn sensors 12 and a cloud based patient specific analysis to dramatically shorten the time to definitive therapy for patients with ischemic stroke.

The system 10 continuously measures natural limb activity and conveys these measurements to a cloud based real-time data processing system 14, which both identifies patient specific alert conditions and determines solutions for acting upon the needs of the specific patient (or user or subject) 100. The system 10 further provides for notification of potential stroke syndromes in real-time and activation of acute stroke protocols. The system 10 also provides the ability to interact with the patient, to assess limb activity, physiology, and cognitive elements (such as audio and visual cues). It is appreciated the present system 10 is particularly suited for those individuals predisposed to the occurrence of a stroke, for example, individuals who have previously suffered a stroke, individuals with high blood pressure, individuals with a family history of strokes, etc.

As will be explained below in great detail, the system 10 relies upon three components:

1) a body worn sensor(s) 12 that is preferably worn on the limb(s) of a patient;
2) a patient worn data transmission device 16; and
3) a cloud based data processing system 14 acquiring information (in the form of data) generated by the body worn sensor 12 and transmitted by the data transmission device 16, analyzing the acquired information, identifying the potential onset of a stroke, and notifying the patient, a patient's caretaker(s), an emergency medical system(s) and/or stroke neurologist(s).

As will be explained below in greater detail, the data processing system 14 performs the step of identifying the potential onset of a stroke by first establishing a patient specific limb activity signature through the aggregation of continuously sampled data acquired over days, weeks and months, and the application of analytical methods as discussed below in greater detail. The system 10 facilitates interaction with the patient and the patient's caretaker(s). Further, the system 10 initiates the steps necessary for the transfer of the patient for rapid evaluation.

Figure 2:
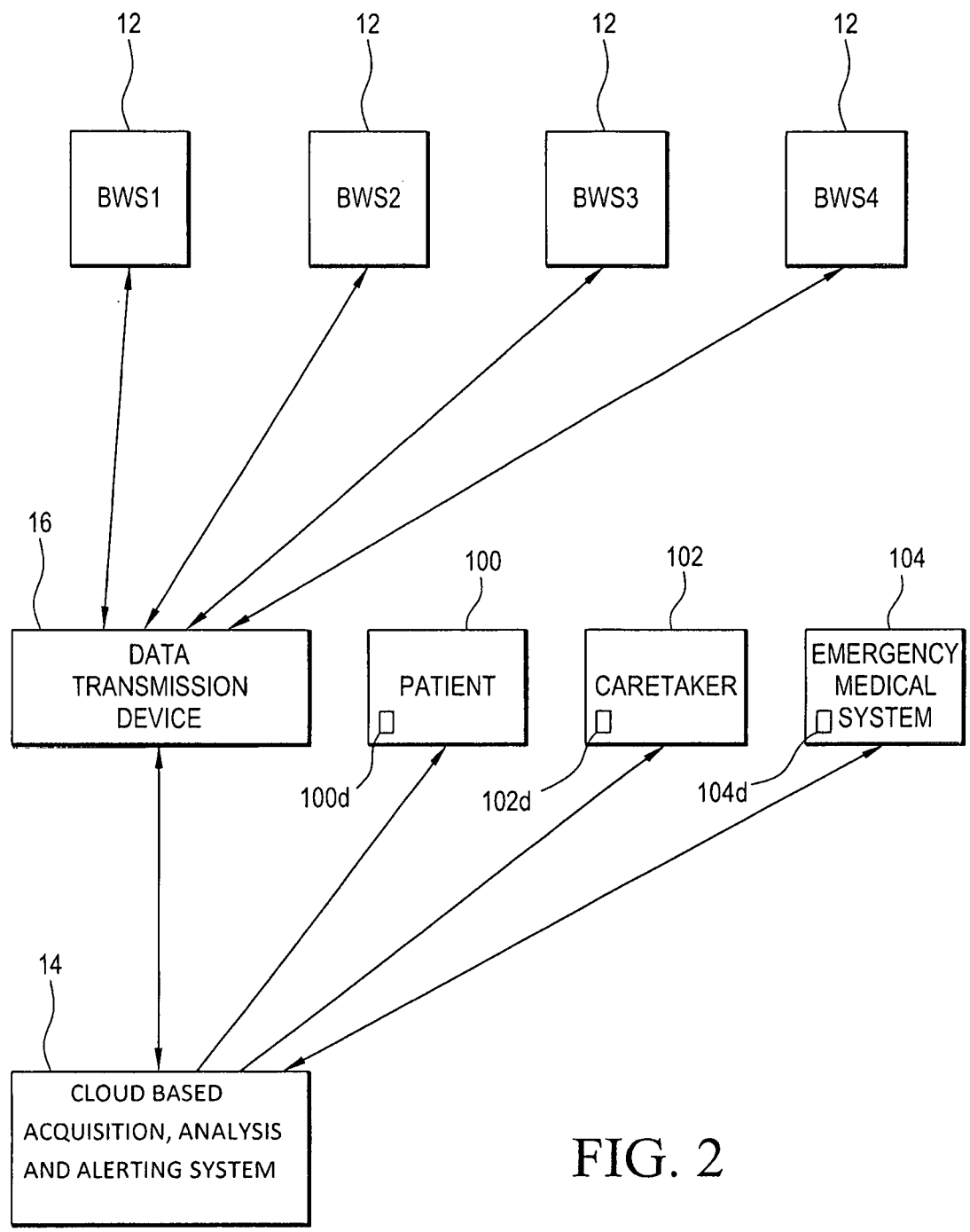

Referring to FIGS. 1 and 2, and as will be explained in greater detail below, the flow of information begins with sensor readings acquired by one or more body worn sensors 12 (referred to as BWS1-BWS4 in FIG. 2). The body worn sensors 12, for example, may be composed of four limb worn sensors 12, as well as other body worn sensors that may be worn on other parts of the body of the patient 100. The data collected by the body worn sensors 12 is relayed to the patient worn data transmission device 16 (for example, a smartphone 35 with a computer software application or "app" 36 operating in accordance with the present invention). A time-stamp is added to this data stream by the patient worn data transmission device 16 and the data from the multiple body worn sensors 12 is compiled into a single data stream. The data is then relayed by the patient worn data transmission device 16 to the cloud based data processing system 14, in particular, the acquisition system 40 of the cloud based data processing system 14.

Cellular and/or Internet communication networks are preferably used to transfer the data from the patient worn data transmission device 16 to the cloud based data processing system 14. With this in mind, it is appreciated there are two ways in which the problem of early detection of stroke may be approached. In accordance with one approach, the environment in which the patient resides is instrumented (that is, the majority of sensors picking up patient activity and functional data transmission components are positioned within the environment in which the patient resides; for example, sensors in the floors, and on the walls, and through cameras and microphones, wherein these sensors would continuously monitor the patient to determine the subject state and level of activity), and continuous readings are made through sensors embedded within the environment, of which continuous readings are then transmitted to the cloud based data processing system 14 for stroke detection. In accordance with a second approach, the patient 100 is instrumented (that is, functional components allowing for data transfer in accordance with the present invention are integrated into the body worn sensors 12 and the patient worn data transmission device 16.

In accordance with a preferred embodiment, and as will be appreciated based upon the following disclosure, the system 10 employs an approach wherein the patient 100 is instrumented; that is, the system 10 provides a solution which is centered around the patient 100, and does not depend on the environment. In this regard, cellular data transmission is the preferred mechanism for data transfer in accordance with the present invention. However, and if the environment does support secure Wi-Fi (a trusted network is detected), then the patient worn data transmission device 16 switches to Wi-Fi when and where it is supported. For the patient 100, the ability to switch to a trusted Wi-Fi network will save data on a cellular plan. It also reduces power consumption and heat generation and increases battery life because Wi-Fi transmission is over a few meters and cellular transmission is over a few km.

In general, the present system 10 is open to both solution strategies; one where the patient 100 is instrumented and one where the environment is instrumented. The solution in which the environment is instrumented will become increasingly more important as nursing homes, rehab facilities, and homes become more instrumented. It is further appreciated that as the system 10 develops, an increasing number of sensors may be available within the environment, and it will be desirable to use data from those sensors in addition to the data from the body worn sensors 12 on the patient.

The acquisition system 40 of the cloud based data processing system 14 adds an additional time-stamp, and conditions the data with nulls if there are missing data samples. With this in mind, it should be appreciated the patient worn data transmission device 16 is a hub between the body worn sensors 12 and cloud based data processing system 14. The patient worn data transmission device 16 always knows which data it has received and which data it has not received from the body worn sensors 12. When data is not received from a particular body worn sensor 12, the patient worn data transmission device 16 indicates this to the cloud based data processing system 14.

The patient worn data transmission device 16 always conveys to the cloud based data processing system 14 how many body worn sensors 12 it is in contact with. For example, patient worn data transmission device 16 is expected to be in contact with body worn sensors 12 worn on the LH (left hand), RH (right hand), LL (left leg), and RL (right leg) of the patient 100, and periodically (currently at the start of each second) informs the cloud based data processing system 14 know that it is in contact with these four body worn sensors 12. That is, at the start of each second the patient worn data transmission device 16 transmits to the cloud based data processing system 14 the codes, for example, LH, RH, LL, RL, to indicate that it is receiving data, respectively, from those four body worn sensors 12.

If a few data samples are not received from a body worn sensor 12, the patient worn data transmission device 16 marks this with a code value in lieu of the data values to indicate those data were missing. If the data stream from a body worn sensor 12 stops (e.g., currently if no data is received for >1 sec), then the patient worn data transmission device 16 indicates this to the cloud based data processing system 14 by updating which body worn sensor(s) 12 it is in contact with. That is, for example, at the top of the next second it indicates that it is in contact with LH, RH and LL body worn sensors 12, and not the RL body worn sensor 12.

The data is then analyzed on the cloud based data processing system 14 and alerts are sent to the patient 100, the patient's caretaker(s) 102 and the emergency medical system(s) 104 as required. Alerts may be sent via text message, email, or other mechanisms to communication devices 100d, 102d, 104d of the patient 100, the patient's caretaker(s) 102 or the emergency medical system(s) 104 in a manner known to those skilled in the art.

Body Worn Sensor

The first part of the system 10 is the body worn sensor(s) 12 shaped and dimensioned to be worn on limb(s) of a patient 100. In accordance with a preferred embodiment, it is contemplated four limb worn sensors 12 are used, wherein the body worn sensors 12 are respectively worn on the left arm (LA), the right arm (RA), the left leg (LL), and the right leg (RL) of a patient 100. As will be explained below in greater detail, the four limb worn sensors 12 each have 9-axis accelerometers. Additional sensors may be used on the body to capture additional information. Further, one or more of the four limb worn sensors 12 also measure galvanic skin response (GSR), heart rate (HR) and temperature (T). The body worn sensors 12 are preferably as unobtrusive as possible. As such, it is contemplated the body worn sensors 12 may be integrated within ordinary objects which are worn on the body such as, but not limited to, clothing, cufflinks, buttons, shoe or belt buckle, ring, bracelet, shoe laces, eyeglass frame and as a patch on the body, including on the chest.

As will be appreciated based upon the following disclosure, detection events indicative of the onset of a stroke are triggered by anomalous data. The primary detection signal is based on anomalous asymmetry in limb activity. The present system 10, however, uses additional sensors such as HR sensors 60, GSR sensors 64 and T sensors 66 to discover other (anomalous) changes which may occur in the peri-stroke period. If these contribute, directly or indirectly, to a detectable difference during the peri-stroke time from baseline, then they are incorporated into the detection process. Though a preferred current approach does not depend on it, all activity is categorized into recognizable states. For example, the system 10 evaluates if it is possible to detect when a person is standing, sitting, or lying down; OR when a person is awake or asleep; OR when a person is indoors or outdoors; In a car (or bus, train), or not; OR when a person is engaged in common tasks such as walking, eating, exercising, getting dressed/undressed. The purpose of this is to improve upon the ability to detect anomalies. The better the system 10 is able to recognize normal states, the better will be the ability to detect anomalies.

Each of the body worn sensors 12 independently and continuously samples limb activity. The signals generated by the body worn sensors 12 are processed to minimize data size, and the signals are then wirelessly communicated to the data transmission device 16.

In accordance with a preferred embodiment, data size is reduced primarily to reduce battery power consumption, reduce transmission cost, and minimize heat generated. Conversely, it is desired to transmit data as close to the full raw sensor data as possible because it is desired that such data should be accessible to analysis programs which run on the cloud based data processing system 14. It is appreciated the data stream for this application is not excessive, and the data bandwidth is managed, for the reasons indicated above, in the following manner:

1) Data is sampled at a low frequency. Patients 100 are often not very active, so the sampling frequency can be, reduced to a low rate. In accordance with a preferred embodiment, the accelerometers are sampled at 40 Hz, and it may be possible to sample at 25 Hz. Modalities such as GSR and T, can be sampled less frequently (for example, they can be sampled once every sec, but this may be further reduced).

2) Data samples are transmitted as raw A/D values, that currently are 2 byte integers, although it is appreciated more than 2 byte integers may be used as the resolution of the sensors improves.

In accordance with a preferred embodiment, all data samples are transmitted. As the characteristics of specific patients are understood through implementation of the present invention, the patient worn data transmission device 16 filters out immaterial data so as to limit the data that is ultimately transmitted to the cloud based data processing system 14. In attempting to optimize battery consumption, heat generation, and data throughput, transmission in bursts may be employed in accordance with the present invention.

The body worn sensors 12 include similar characteristics and a single representative body worn sensor 12 is described below. With this in mind, the system 10 may include various arrays of body worn sensors; for example, it may be desirable to provide limb worn sensors to pick up limb activity, and then additional sensors on one or two limbs, or another location such as the chest, or ear, where HR, GSR and T are measured and detected. The patient worn data transmission device 16 includes a microphone 16a and a camera 16b, and is used to also pick up audio (the person speaking) and video/snap shots of the person's face if necessary.

Figure 3:
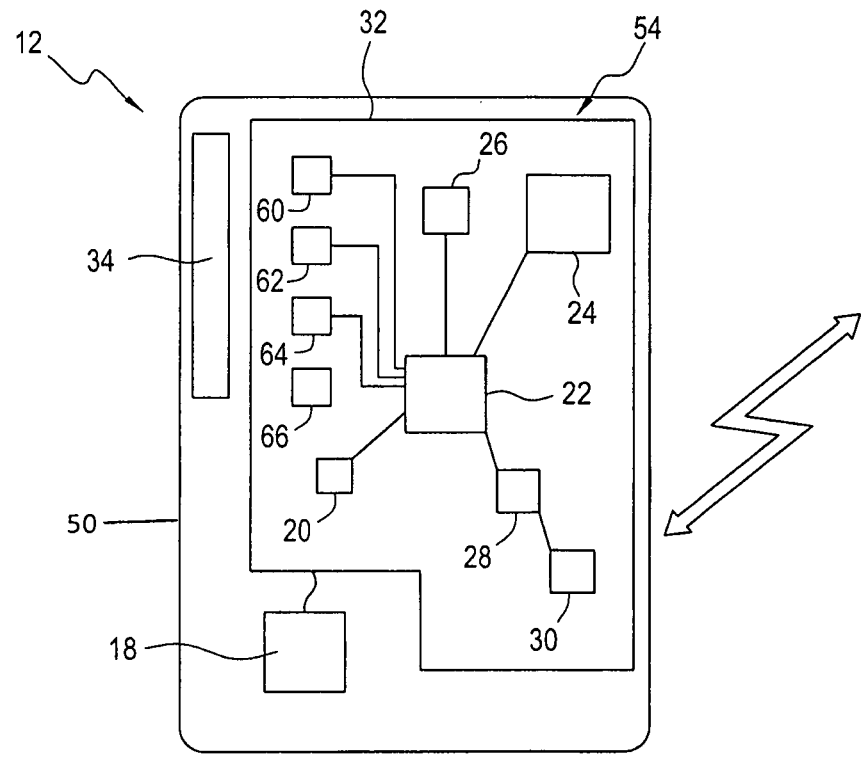
FIG. 3 is a schematic showing the housing and sensor electronics of a body worn sensor in accordance with the present invention.
Figures 4A, 4B:
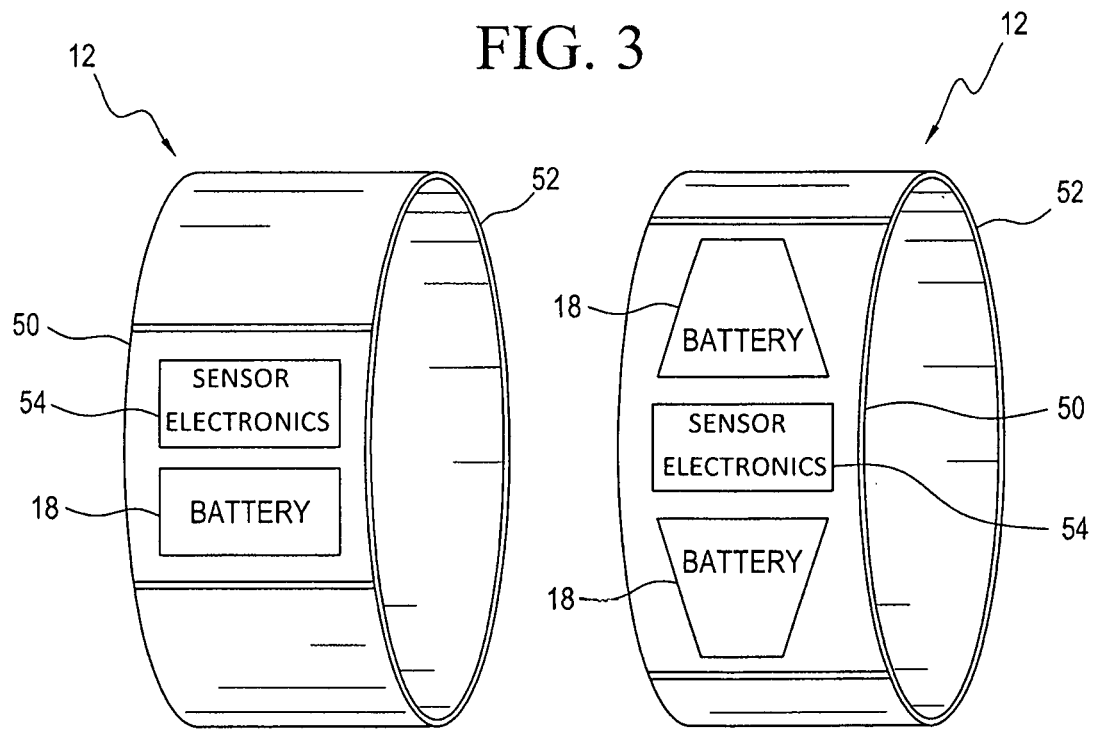
FIGS. 4A and 4B are schematics of first and second embodiments of the body worn sensor.
Figure 5:
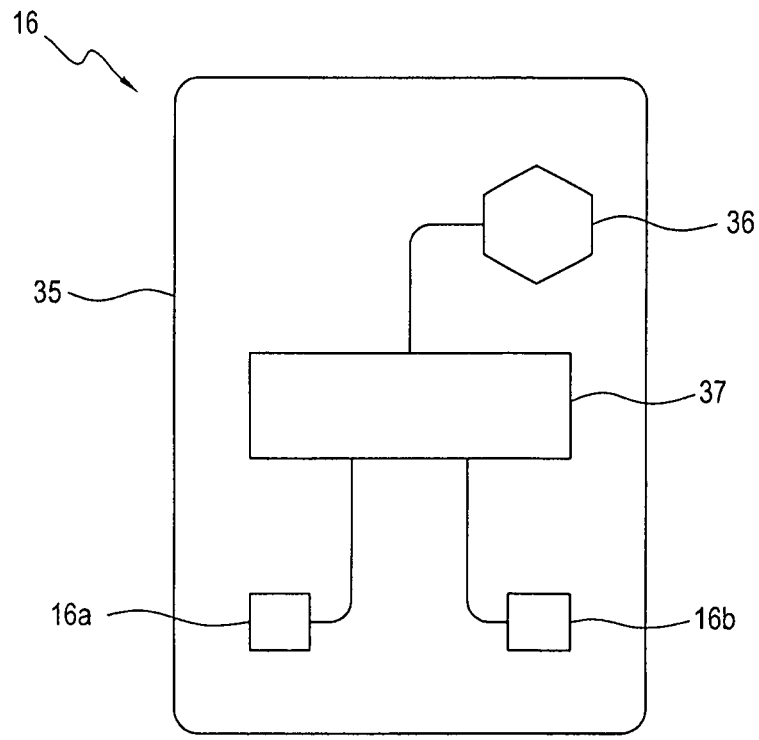
FIG. 5 is a schematic of a patient worn data transmission device in accordance with the present invention.
Figure 6:
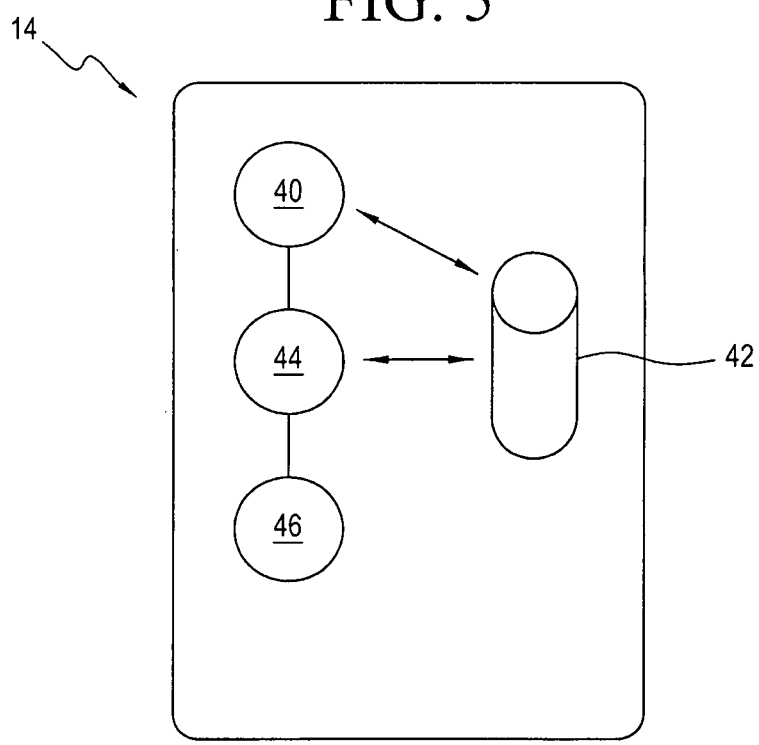
FIG. 6 is a schematic of a cloud based real-time data processing system in accordance with the present invention.

The body worn sensor 12 is constructed to continuously identify limb position in conjunction with the duration of limb movements, and the speed of limb movements (or otherwise referred to herein as "limb activity"). Referring to FIGS. 3, 4A and 4B, the body worn sensor 12 includes a housing 50 for electronics associated therewith and a strap 52 for wrapping about the limb of the patient 100. In particular, sensor electronics 54 and a power source 18 (in the form of a battery, wherein the first embodiment shown in FIG. 4A includes a single battery 18 and the second embodiment shown in FIG. 4B includes dual batteries 18) are stored within the housing 50. The sensor electronics 54 include a clock 20, a data processor 22 (for example, a microcontroller) controlling operation of the body worn sensor 12, a 9-axis motion tracking device 24, a pressure sensor 26, a signal processor 28 continuously processing signals generated by the 9-axis motion tracking device 24, and a wireless communication protocol (or module) 30 (for example, Bluetooth Low Energy) continuously transmitting signals to the data transmission device 16.

In addition to these elements, other sensor elements may be employed in conjunction with (or integrated with as is shown in FIG. 3 in accordance with a preferred embodiment) the body worn sensor 12. Such additional sensor elements may be worn on the limbs (in conjunction with the body worn sensors 12 described above, on the torso or on the ear. The additional sensors may include, but are not limited to, a heart rate (HR) monitor 60, A 1 or 2 lead EKG (electrocardiogram) 62 (which would necessarily be worn on the torso), a galvanic skin response (GSR) monitor (an electrodermal activity or skin conductance monitor) 64, a body temperature (T) monitor 66, a sweat analysis monitor, a hydration monitor, a muscle tautness monitor, a blood composition monitor (achieved through spectrometry), a sleep monitor, an audio monitor, a video monitor and/or other monitoring devices that might provide information useful in the detection of the onset of strokes and other acute central nervous system injuries.

More particularly, and in accordance with a preferred embodiment of the present invention, the data processor 22, 9-axis motion tracking device 24, signal processor 28, wireless communication protocol (including an antenna) 30, and other sensing devices are integrated into a single printed circuit board 32. Preferred elements for the present body worn sensor 12 include a power source 18 in the form of a flexible thin film battery (it is also contemplated the power source may be in the form of a flexible thin film solid state battery). The 9-axis motion tracking device 24 is preferably composed of the InvenSense MPU-9255. The InvenSense MPU-9255 combines a 3-axis gyroscope, 3-axis accelerometer, 3-axis magnetometer and a digital motion processor to produce an output signal indicating the position and orientation of a limb to which the body worn sensor 12 is attached. Further, the data processor 22 is preferably composed of a low power microcontroller unit and a wireless communication protocol 30, for example a Bluetooth Low Energy transceiver. Still further, the body worn sensor 12 includes an LED interface display 34 having a touch screen allowing for various tap gestures used in the operation of the present body worn sensor 12. In accordance with a preferred embodiment, the communication between the body worn sensors 12 and patient worn data transmission device 16 is performed over Bluetooth Low Energy (BLE). The communication follows the BLE 4 GATT data protocol. In the future it is anticipated this will change to BLE 5, or other communication protocols that may become available. BLE 5 will make greater bandwidth and security available. The data are transmitted from the sensors to the phone app in a data stream of 16 bit (2 byte) words. In the patient worn data transmission device 16, the different sensor data streams are combined into one data stream, and a time-stamp is added.

Data Transmission Device

As briefly mentioned above, the data transmission device 16 continuously samples the body worn sensor(s) 12, compiles the sensor data into a single synchronized data stream, and transmits the data to the cloud based data processing system 14. It is appreciated that while the body worn sensor and the data transmission device are disclosed herein as separate and distinct components, these components could be combined into a single unit.

The data structure holds 1-sec of data as follows:
- At the top of each second a header with a timestamp and a set of codes to indicate which body worn sensors 12 (that is, the body worn sensors 12 of the LH, RH, LL, RL) and modalities are recorded.
- Following this, the data samples are recorded by the different body worn sensors 12. If sampling occurs at a rate of 40 Hz, then a set of data samples is received from each body worn sensor 12 every 25 msec. If sampling occurs at a rate of 25 Hz, then a set of data samples is received from each body worn sensor 12 every 40 msec.
- Each set of these data samples has the following structure:
  <x1><y1><z1><x2><y2><z2><x3><y3><z3>
  Here:
  <x1><y1><z1> are the three acceleration readings
  <x2><y2><z2> are the three gyroscope readings
  <x3><y3><z3> are the three magnetometer readings.
  As indicated above, each of the data samples <x1> or <y1> etc. is a 2-byte word.
- In addition to this, the accelerometer (not shown) within the patient worn data transmission device 16 (that is, the accelerometers the are conventionally included in smartphones 35) is also sampled. This may be a 3-axis, 6-axis or 9-axis accelerometer.
- The body worn sensors 12 which are sampled only once per sec, for example, GSR sensors 64 and T sensors 66, are stored at the end of the 1-sec record.
- Finally, a set of flags and data values indicate the state of the communication of this data to the cloud based data processing system 14. This indicates the number of times an attempt has been made to transmit the data to the cloud and information on the communication used (cellular, Internet, network).
- Other modalities, e.g., audio via the microphone 16a, video via the camera 16b, and GPS are processed in separate data streams (as supported by the operating system of the patient worn data transmission device 16) and are collected when needed.
- The battery state and strength of communication between the body worn sensors 12 and the patient worn data transmission device 16 is embedded within the data stream and transmitted to the cloud based data processing system 14 every minute.
- Once a set of data have been successfully received by the cloud based data processing system 14, they are deleted from the body worn sensors 12 and the patient worn data transmission device 16. In particular, the data from the body worn sensors 12 are deleted when received by the data transmission device 16 and the data from the data transmission device 16 is deleted when received by the cloud based data processing system 14.

The data transmission device 16 further provides a time-stamp regarding the date and time of the limb activity, and associates the time-stamp with the data as transmitted in accordance with the present invention. While the time-stamp as discussed herein takes place in the data transmission device 16, it is appreciated the data may also (or alternatively) be time-stamped as it is developed at the body worn sensor 12 or in the cloud based data processing system 14.

In accordance with a preferred embodiment, the data transmission device 16 is preferably a smartphone 35 employing an "app" 36 to achieve data transmission in accordance with the present invention, as well as electronics 37 commonly employed in a smartphone 35. In accordance with a preferred embodiment, the smartphone operates under Apple's iOS operating system or Google's ANDROID® operating system. It is also appreciated tablets or other similar electronic devices may be used instead of smartphones. In the event of a notification regarding the onset of a stroke or notifications regarding other elements of the present system 10, the smartphone 35 is also be used as the contact mechanism for communicating with the patient. Although a smartphone is disclosed for use in accordance with the present invention, it is appreciated other data transmission devices may be employed without departing from the spirit of the present invention.

Cloud Based Data Processing System for Acquisition, Analysis and Alerting

The third part of the system 10 is preferably a HIPAA (Health Insurance Portability and Accountability Act) compliant cloud based data processing system 14 acquiring and processing the data streamed from each patient 100. The cloud based data processing system 14 detects, using a patient specific database and a powerful time-series analysis method, patient specific limb activity signatures representative of weakness due to stroke. It is appreciated that the time-series analysis method employed in accordance with the present invention could be supplemented by adding any number of direct or indirect measures where such measures are determined to improve the performance of the time-series analysis method. While limb activity data is the primary measure employed in the analysis method, other sensor modalities, for example, audio, video, heart rate, temperature, etc.), may be employed in identifying the onset of a stroke.

Based upon patient specific limb activity signatures, the cloud based data processing system 14 identifies the likely onset of a stroke, that is, an alert condition, and initiates protocols for subsequent interaction with the patient, or the patient's caretaker(s). The interaction with the patient 100 may include acquisition of audio or video/snap-shots. The audio is analyzed to determine changes in speech. The video/snap-shots are analyzed to determine changes in facial muscles indicative of stroke. The cloud based data processing system 14, in conjunction with the identification of the likely onset of a stroke (or other acute central nervous system injuries, also initiates related treatment protocols, for example, activation of the emergency medical response system, the transport of the patient to the nearest Neuro-critical Care Unit or emergency room for rapid evaluation and treatment.

The cloud based data processing system 14 is composed of three parts: an acquisition system 40; an analysis system 44; and a patient management system 46.

Acquisition System

The acquisition system 40 of the cloud based data processing system 14 compiles all the streaming data generated by the body worn sensor(s) 12 and transmitted by the data transmission device 16. For each patient 100 being monitored in accordance with the present system 10, the generated data is stored in a patient specific database 42. In conjunction with the compilation of the generated data, the acquisition system 40 also determines connectivity of the body worn sensor(s) 12 and the quality of acquired data. In accordance with a preferred embodiment, the compilation of the generated data and the determination of sensor connectivity are achieved by sampling the time-stamped data sent by the data transmission device 16, identifying gaps in the data, and formatting the data for further processing. For example, the 9-axis motion tracking device 24 of the body worn sensor 12 continuously samples limb activity. The 9-axis motion tracking device 24 reads out three 16-bit gyroscope outputs (to detect rotation about the X-, Y-, and Z-axes), three 16-bit accelerometer outputs (to measure acceleration along the X-, Y-, and Z-axes), and three 16-bit magnetometer outputs (for detecting terrestrial magnetism in the X-, Y-, and Z-axes). Limb activity is determined from these nine measurements. The output of the 9-axis motion tracking device 24 is nine 16-bit words (that is 18 bytes) for each acquired sample. Current sampling is at 40 Hz; that is, 40×9×18 bytes per second are generated. This data is streamed from each limb worn sensor 12 to the data transmission device 16. It is appreciated that the sampling frequency is adjusted to optimize power consumption and capture of salient aspect of limb activity. It is further appreciated other sensors may be added within the body worn sensors, and other sensors which are placed on the torso (for example, EKG sensors 62) or elsewhere on the body may be incorporated into the present system 10.

This data, with the flags and time-stamp, is transmitted to the cloud based data processing system 14 where it is processed for further analysis in accordance with the present invention. It should, however, be appreciated the movement analysis is performed in the second step (i.e. in the analysis system 44 as described below). The process performed by the acquisition system 40 is straightforward in that the acquisition system 40 time-stamps the received data, and merges it with the previously acquired data.

With the foregoing in mind, operation of the acquisition system 40 may require an evaluation of continuity, and introduction of blanks (or NaNs) as filler data. In addition, the acquisition system 40 flags a patient's data stream for being discontinuous if there are many gaps in the stream. If the data are flagged in this manner, then that information is relayed back to the patient to help trouble shoot data connectivity and used to determine if the data should be analyzed by the analysis section.

As indicated above, detection events for the identification of the onset of a stroke are triggered by the detection of anomalies in the data. By this it is meant that the system 10 has an expectation of the signal characteristics for a given patient and deviations from this expectation are of interest as they may represent an event of interest, in particular, the onset of a stroke. All anomalies in the data stream are identified and analyzed. Any change in the data triggers a set of responses geared to understand why the change has occurred. This set of evaluations includes ruling out technical issues as a cause for the observed change (for example, it could be that the system 10 could suffer a loss of communication from the body worn sensors 12 to the smartphone 35, or from the smartphone 35 to the cloud based data processing system 14, or from the cloud based data processing system 14 to the patient 100; it could also be the case that this loss of one or more links could be due to technical reasons, and may have no implication on the health of the patient 100; or, it could be that that loss is reflective of an important change in patient state, beyond the technical issue, for example, a fall could jar a wrist worn sensor 12 loose, in which case it would transmit non-physiological data, or break it, in which case connection with the sensor 12 would be lost). Ultimately, the cloud based data processing system 14 builds a collection of analyzed, high quality data for each patient 100.

Analysis System

The data acquired is continuously analyzed using the analysis system 44. The system 10 tracks an ensemble of diffusion geometry measurements and other time-series measures of signal magnitude, variability, complexity and interrelation determined from the measurements of the body worn sensor 12. The system 10 continuously matches ensembles of measurements from limb movement to detect disruption of symmetry, and track as well ensembles of measurements built from HR, GSR and T and other sensor modalities to detect anomalies. In accordance with the present invention system 10, the analysis system 44 employs the data processing methods developed by Professor Ronald Coifman of Yale University. These methods are described in Coifman, R. R. and S. Lafon, Diffusion maps. Applied and Computational Harmonic Analysis, 2006. 21(1): p. 5-30, Coifman, R. R., S. Lafon, A. B. Lee, M. Maggioni, B. Nadler, F. Warner, and S. W. Zucker, Geometric diffusions as a tool for harmonic analysis and structure definition of data: Diffusion maps. Proceedings of the National Academy of Sciences of the United States of America, 2005. 102(21), and Talmon, R., S. Mallat, H. Zaveri, and R. R. Coifman, Manifold Learning for Latent Variable Inference in Dynamical Systems. IEEE Transactions in Signal Processing, 2015, all of which are incorporated herein by reference.

Employing the diffusion mapping processes developed by Professor Coifman, the analysis system 44 continuously processes limb activity and sensor data, and determines, in comparison to a previously determined patient specific limb activity signature if the current limb movements of the patient 100 are within expected parameters. The activity of major muscle groups and the nervous system control of these muscle groups are quantified through the present system 10. This is accomplished by quantifying the geometry of the dynamics of the motion of limbs of a patient. Multi-dimensional representations of limb activity are built using diffusion maps, and the differences between a pre-established multi-dimensional representation of limb activity (that is, the patient specific limb activity signature) and a current multi-dimensional representation of limb activity are evaluated to identify changes from baseline (that is, the patient specific limb activity signature). If the limb activity is not within expected parameters (that is, the current activity is not consistent with the patient specific limb activity signature) then an alert is generated. Diffusion geometry enables precise quantification of distance between data clouds (that is, distance between ensembles of measurements characteristic of a patient). The system 10 has precise statistical measures of the differences between ensembles of measurements, these measures are designed to test the hypothesis that a patient 100 conforms to his own normal model, and where measurements do not conform to the patient's normal model the anomaly is documented and appropriate action is taken. In accordance with a preferred embodiment, the alert is issued within a time-window of 10-20 minutes. However, it is appreciated that it is possible that in the case of the introduction of subtle deficits in limb activity that the time to alert may be longer, as it may take longer for the analysis system 44 to detect the deficit in limb activity. It is also possible, that in the case of sedentary patients that the analysis system 44 will take longer to raise an alert; once again, long determination times will be a result of the difficulties in definitively determining when an alert condition has been crossed.

More particularly, as to identifying anomalies indicative of the onset of a stroke, that is, the analysis leading to a determination of a patient specific stroke condition, the system 10 continuously quantifies limb activity, creates patient specific limb activity signatures, and compares real-time limb activity to a patient specific limb activity signature for the identification of anomalies that may be indicative of the onset of a stroke other acute central nervous system injuries. Where anomalies are detected alert conditions are identified and (as is described below with regard to the patient management system 46) alerts are initiated and action is taken.

As has been discussed above, the analysis system 44 develops limb activity signatures which are specific for each patient 100. These patient specific limb activity signatures are continuously compared against current patient behavior. In the event that a patient 100 has a deficit in limb activity introduced by a stroke, the previously established patient specific limb activity signatures can also be used to quantify the degree of success in restoring function during rehabilitation.

As briefly described above, this analysis relies upon analytical methods of Prof. Coifman for the analysis of sensor signals using diffusion maps. Diffusion maps are a dimensionality reduction and feature extraction algorithm. Briefly, the Eigen functions of a Markov matrix defining a random walk on the data are used to obtain new descriptions of data sets via a family of mappings that it is termed "diffusion maps." These mappings embed the data points into a Euclidean space in which the usual distance describes the relationship between pairs of points in terms of their connectivity. This defines a useful distance between points in the data set that is termed "diffusion distance." The approach employed by Coifman generalizes the classical Newtonian paradigm in which local infinitesimal rules of transition of a system lead to global macroscopic descriptions by integration. Different geometric representations of the data set are obtained by iterating the Markov matrix of transition, or equivalently, by running the random walk forward, and the diffusion maps are precisely the tools that allow the spectral properties of the diffusion process to be related to the geometry of the data set. In particular, one does not obtain one representation of the geometry for the set, but a multiscale family of geometric representations corresponding to descriptions at different scales.

As such, and in accordance with the present invention, data generated based upon patient limb activity is applied to create a multi-dimensional diffusional map as taught by Coifman. When this multi-dimensional diffusion map is created using data during normal, health movement, the multi-dimensional diffusion map defines a patient specific limb activity signature. This patient specific limb activity signature is then continuously compared with similar diffusion maps based upon real-time limb activity for the identification of anomalies indicative of the onset of a stroke. Anomalies are detected when the diffusion map based upon real-time limb activity deviates from the patient specific limb activity signature by a pre-established extent.

The ability to apply the diffusion mapping methodology to the present system 10 based upon identified anomalies in limb activity has been proven by collecting data from patients and normal volunteers, including using it to differentiate between runners based on the movements of their limbs and the development of a cloud based data acquisition system and real-time analysis system.

In particular, two experiments were performed. The first experiment was performed on 11 individuals. These 11 individuals consisted of 6 normal subjects (5 female, age range 29-51 years, all right hand dominant), and 5 patients who had recently suffered a right hemisphere stroke (3 female, age range 47-86, 3 right and 2 left hand dominant). The NIH Stroke Scale/Score (NIHSS) was evaluated for the 5 patients before the study and was 11, 9, 1, 5, and 2. The left and right arm strength was evaluated and was 0/5, 0/5, 4/5, 4/5, and 4/5 for the left arm and 4/5, 5/5, 5/5, 5/5, and 5/5 for the right arm (the stroke patients all had left side weakness). The 11 individuals wore a 3-axis accelerometer both on the left-hand and the right-hand. While wearing the sensors, participants were asked to perform a neurological exam, consisting of specific motions, for the purposes of obtaining standardized data. These motions followed elements of the neurological exam, with attention to motor strength, movement in planes, and gait. Also included were tasks such as lift your arms up for 10 seconds, simulate washing your hands in the sink, simulate drying your hands with a towel, and flip your palms up and down 5 times.

Acceleration data was collected during the performance of the tasks. The accelerations in the X, Y and Z axes for each hand was measured. The acceleration data were sampled at 25 Hz. The data were evaluated with different time-series analysis measures. Two sets of results are shown here to demonstrate the separation of the normal subjects and the stroke patients. First, in FIG. 10, the average absolute acceleration for the left hand and right hand for each individual tested is presented. The average absolute acceleration was first averaged separately for each of the three axes studied, and then an average was calculated for the three axes. The data used here were collected when the individuals were performing a simple task "cross your arms over each other five times". The average absolute acceleration values for the 6 normal subjects and 5 stroke patients are shown in FIG. 10. A linear classification boundary was estimated and is displayed. The linear classification boundary indicates that there is a complete separation between the data from the stroke patients and normal subjects. In FIG. 11 the diffusion maps analysis of acceleration data from two normal subjects and two stroke patients while they performed a second task "cycle your fists in front of you" is presented. The diffusion maps demonstrate a clear capture of the dynamics of the hand movement, and the difference between the stroke patients and the normal subjects. Both a simple measure of magnitude, the average absolute acceleration, and the diffusion maps have been included to underscore the following. It is possible that a number of time-series measures can be used to distinguish between patients and normal subjects. However, to create limb specific signatures more powerful methodology is needed to capture the dynamics of limb activity. The first method employed removes all information on the dynamics of limb activity, to obtain the average absolute acceleration value. This is sufficient to achieve a separation between patients and normal subjects, and thus is of value. The second method, diffusion maps, however, is a more powerful method which allows capture and quantification of the rich dynamics of these data and thus can further extend the analysis which is performed by the simple time-series measures. The ability of the diffusion maps algorithm to create limb specific signatures is illustrated through the second experiment described below.

In the second experiment, acceleration and rotation data was gathered from the wrist and ankles of thirteen runners at speeds 5 and 7.5 on a treadmill, and this data was used in conjunction with the diffusion maps feature extraction technique to identify unique characteristics between runners. Upon computing the diffusion map embedding for pairs of motion datasets, similarities between runners were computed by comparing their ergodic measures.

Thirteen volunteers (eight males, five females) between the ages of 18-22 were asked to run on a treadmill and produce motion data. The same treadmill was used for each trial for sake of pace consistency. Devices running a motion measurement app were strapped to each runner's right ankle and wrist. The workout is described below:
  1 minute warmup, running at a speed of 6 mph (mile per hour) (no data collection)
  30 second rest.
  1 minute workout, running at a speed of 5 mph (data collected)
  30 second rest.
  1 minute workout, running at a speed of 7.5 mph (data collected)

Motion data samples were taken at 100 Hz, where each sample consisted of a 12-dimensional vector (6 values per ankle and wrist). Each workout consisted of two trials, one at a speed of 5 mph and one at a speed of 7.5 mph. A trial was defined to be the time series of 12-dimensional vectors at a given speed. Among the thirteen runners, five performed more than one workout, and the remaining eight performed only one workout, resulting in 40 total trials. Each trial generated a single dataset, for a total of 40 datasets.

Diffusion maps were created and used to reduce the high dimensional datasets obtained from individual runners and attempt to extract relevant features to distinguish between them. From this similarities between motion datasets generated from the same person were detected. A novel algorithm was thereafter generated that combines diffusion maps for dimensionality reduction of a dataset and uses a generalization of the earth mover's distance as a similarity metric to compare datasets. Generally, this algorithm considers the various diffusion maps by applying eiginfunctions to the data and creating a broad representation diffusion map. With the plurality of diffusion maps generated in this manner, overlaps are identified and correlations are determined. For a given runner, the algorithm successfully found correlations between motion data at a speed of 5 mph with motion data at a speed of 7.5 mph for the same runner, and correlations also held for a given runner at the same speed over multiple workouts.

Figure 7:
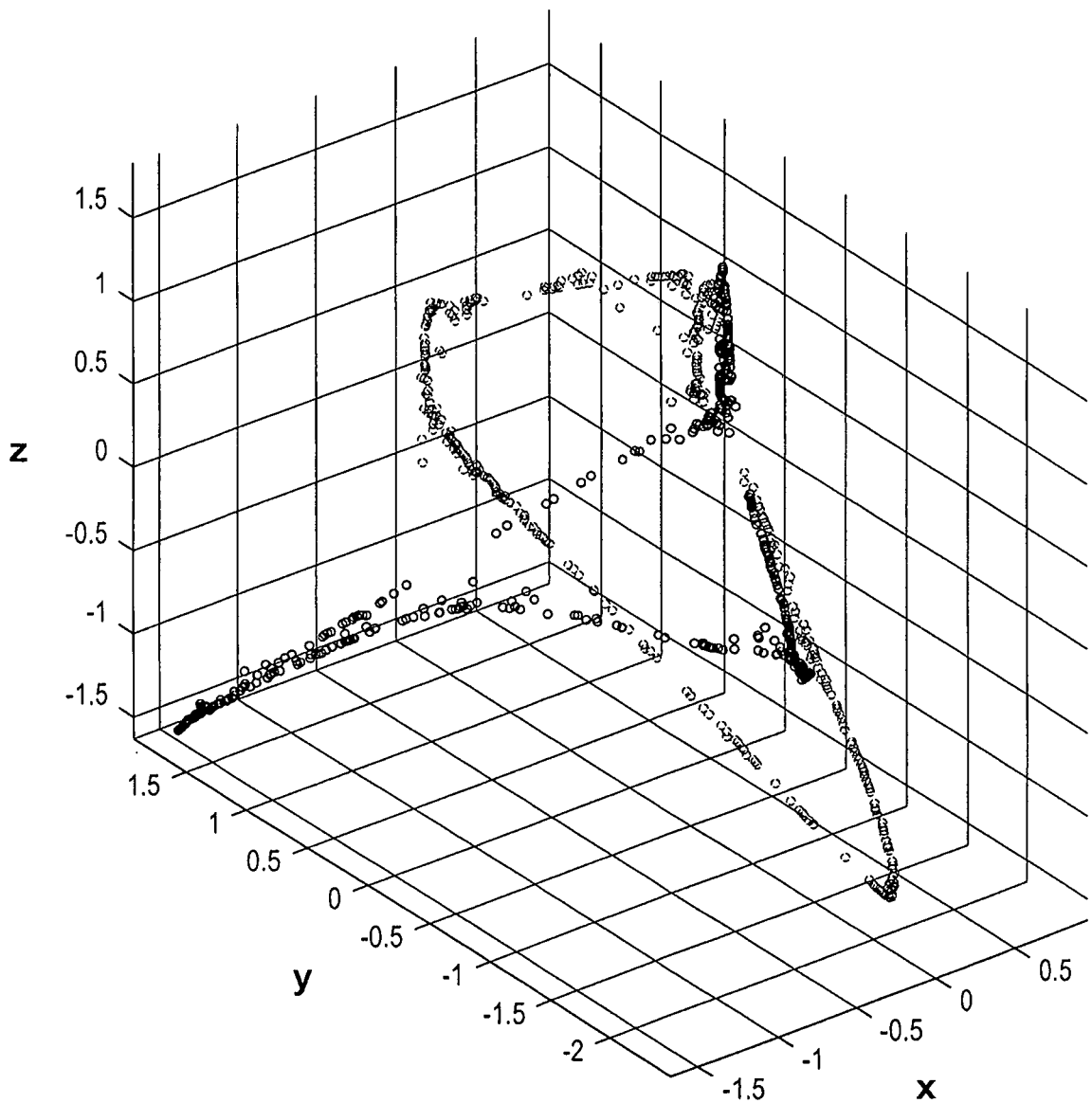
FIG. 7 shows diffusion maps of a pair of trial datasets for different runners.
Figure 8:
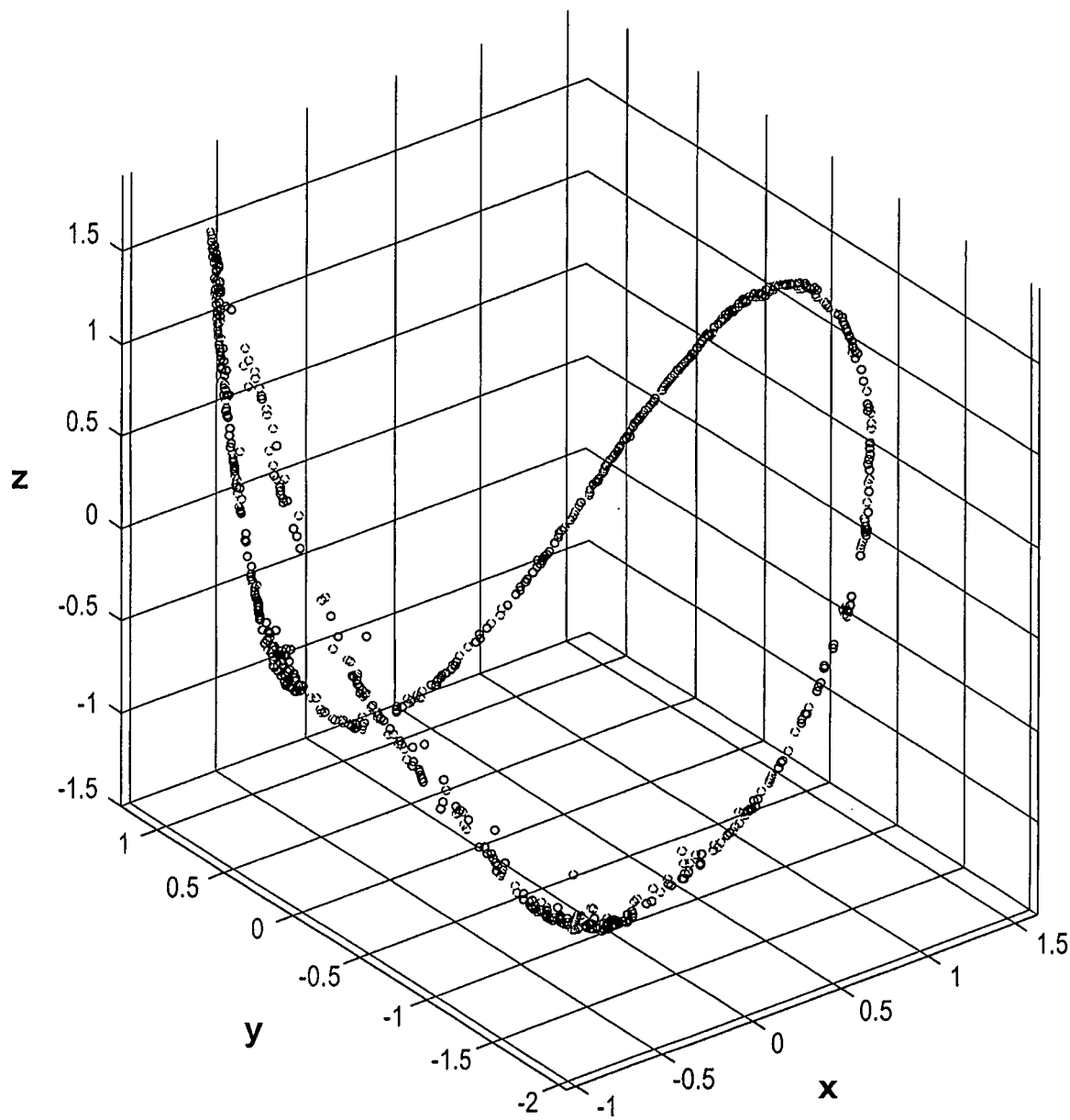
FIG. 8 shows diffusion maps depicting two trajectories produced by the same runner.

After applying the diffusion map algorithm to a pair of trial datasets, it was possible to visualize comparisons between trials by plotting the three most significant embedding vectors in MATLAB and coloring points in the embedding based on which original dataset they correspond to. Obvious differences between the trajectories of different runners, and trajectories produced by the same runner were observed by way of this technique. In FIG. 7, it is evident that distinct Runners 3 and 11 have vastly different running patterns, based on both the visual disparity in the scatter plot as well as the large distance between their ergodic measures, d=1.0548. On the other hand, FIG. 8 depicts two trajectories produced by the same runner at a speed of 7.5 mph that are much more similar both in appearance as well as the small distance between them, d=0.0599. Note that between trials, Runner 10 was given a period of rest and had the motion measurement devices re-strapped between trials, yet still exhibited high correlation across runs.

Figure 9:
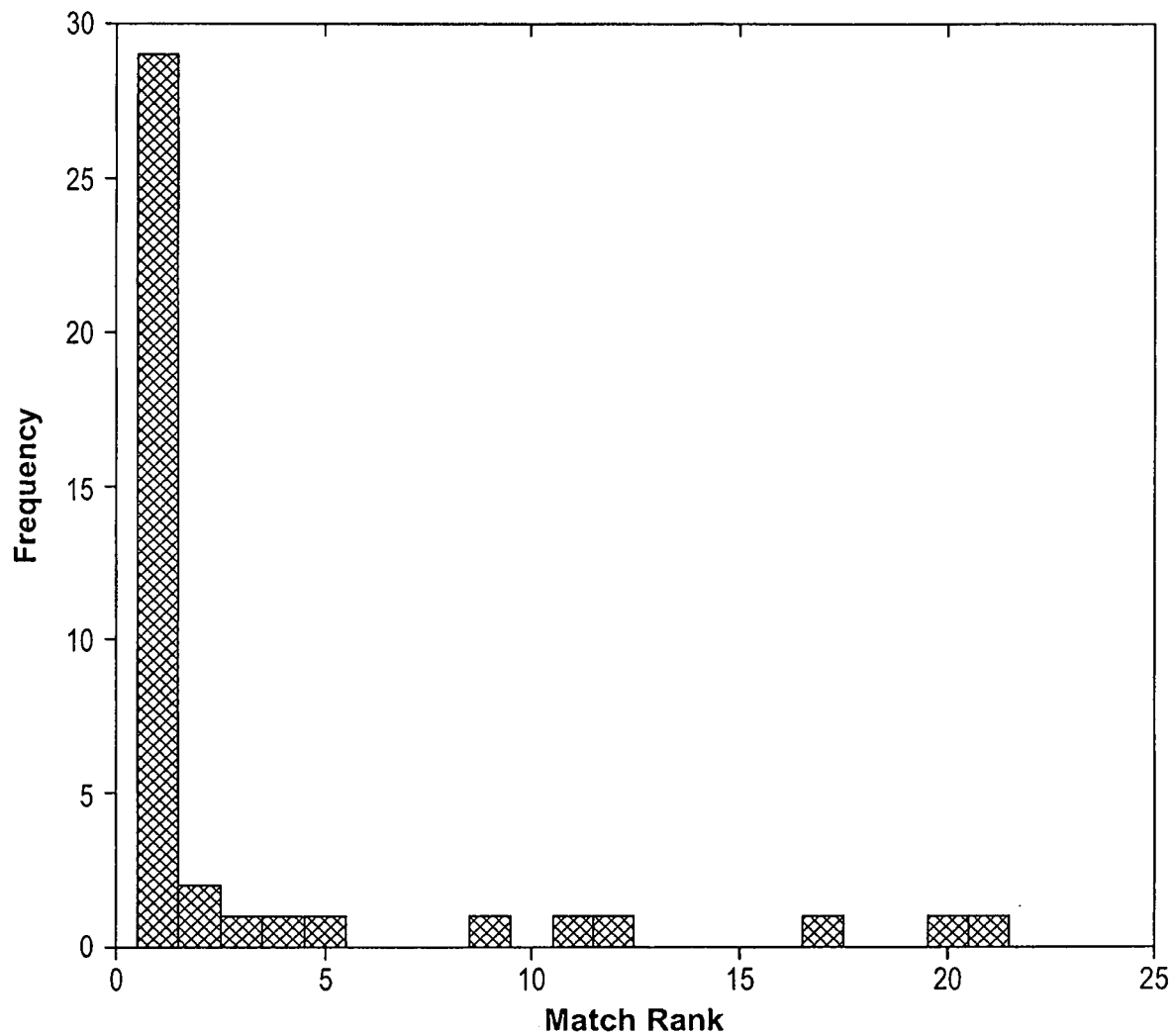
FIG. 9 is a chart comparing various trials from runners.

The most striking result of the study was that an individual runner's motion data at a speed of 5 mph is correlated with the same runner's motion data at a speed of 7.5 mph. Most of the runners ran only one workout, producing one dataset at a speed of 5 mph and one at a speed of 7.5 mph, and in the analysis, all datasets from both speeds were combined. A MatchRank measure was created to compare the similarity of the different trials. When MatchRank=1, the data from a patient is matched to data from the same patient in a pairwise comparison. Most pairwise comparisons return a MatchRank value of 1. That is each trial from a runner is being matched to another trial from the same runner. Frequency charts were created of MatchRanks producing compelling results displayed in FIG. 9. This method was able to produce a MatchRank of 1 in 29 out of 40 trials, for a success rate of 72.5%. Hence, many of the MatchRank values shown in FIG. 9 are 1 as result of a runner's speed at the 5 mph trial being matched with the speed at the 7.5 mph trial, indicating some underlying "running style" that is unique to an individual runner, even across varying speeds.

As with any experiment involving physical measurements, it is appreciated that inaccuracies in the data collection process may lead to error. Most notably, it was impossible to standardize device orientation across trials because the devices were strapped on by hand. Second, the fact that runners had smartphones strapped to their limbs also probably had a disruptive effect on their natural running patterns. Lastly, the motion sensing hardware was inconsistent as both an iPhone 5c and iPhone 4s were used to collect motion data. However, because of the minor physical differences between the two smartphone types and the fact that both smartphones ran the identical motion measurement app, it is believed the impact on the data is negligible.

By performing analysis of motion data, it was shown that individual runners exhibit unique features that are expressed through the acceleration and rotation of their wrists and ankles while running. The runner comparison algorithm involving diffusion maps and ergodic measures achieved a high success match rate. In addition to the runner comparison algorithm, an iPhone motion measurement app was produced to collect motion data, as well as extensive MATLAB code implementing the algorithm and data analysis techniques described. The iPhone app captures limb activity data using the sensors built into the phone, places a timestamp into the data stream, and continuously transfers the time-stamped data to the cloud. The data on the cloud are continuously analyzed using the methods described above and a quantification of limb activity data is produced in real-time.

This experiment demonstrates clear success in determining a specific limb activity signature for each individual based on diffusion map analysis of ankle and wrist activity data. For the present system 10 it is noted that data is aggregated from multiple days and weeks of monitoring, to build a detailed patient and limb specific activity signature. The limb activity signature consists of a continuously updated activity map of the patient's limb activity. The signature is qualified by patient state, time of day, time of year, and geographical location. Deviations from this activity map are continuously obtained using a running window over past activity. The running window is compared to the signature. Deviations of the measurements within this running window are qualified by the magnitude of the deviation and the duration of the deviation. The length of the running window is determined for each patient. The running window is expected to be 10 minutes in duration for most individuals. For more sedentary individuals a longer running window is used.

Ultimately, the evaluations are performed in three distinct manners. First, the evaluations are performed in the ward on patients who have recently suffered a stroke. These patients are studied over a few days while they are in the hospital. The limb asymmetry in these patients is resolved, to a degree, over the duration of their stay in the hospital. This restoration of function is measured, towards baseline. The time-line is then reversed and these measurements are used as a surrogate to develop the asymmetry signature, and quantify the magnitude of the deficit which results from a stroke. Second, patients are tested at a neuro-rehabilitation center. These are patients who have had a stroke. Patients are at the greatest risk of a subsequent stroke in the first 90 days after a stroke. These patients are measured in a controlled environment 24 hours/day for 90 days. Third, individuals are tested in their natural environment. In the second and third distinct manners for evaluation the goal is to detect stroke occurrence in near real-time (within 10-30 minutes of the occurrence of a stroke).

Patient Management System

In conjunction with data developed by the acquisition system 40 and the information generated by the analysis system 44, the patient management system 46 identifies anomalies indicative of patient specific alert conditions. Upon the identification of a patient specific alert condition, the patient management system 46 performs various functions.

In particular, and most importantly, the patient management system 46 directly interacts with the patient 100 to notify the patient 100 that a patient specific alert condition has been detected. In accordance with a preferred embodiment, and as mentioned above, the patient is contacted via the communication device 10d, which in accordance with a preferred embodiment may be the smartphone 35 that is also functioning as the data transmission device 16.

The first contact with the patient 100 is used to determine if there are any untoward situations which have arisen, which resulted in the alert condition. This first contact is used to rule out conditions such as non-working body worn sensors 12, or if the patient 100 has been unusually still for any reason other than normal behavior. The patient 100 is asked to perform a standard movement with each set of limbs. This standard movement task could be as simple as standing up and raising each arm. This interaction allows the operator of the system 10 to determine the responsiveness of the patient 100, and score their response to a standard test, akin to a neurological exam. Additional evaluations may include analysis of audio and of facial muscles to detect changes reflective of stroke.

Once it is determined that further action is necessary or if the system 10 fails to achieve interaction with the patient 100, the patient's caretaker(s) 102 is notified. The caretaker(s) is provided with detailed information on patient location, alert condition, the time of the attempt to interact with the patient, and the result of the attempt to interact with the patient. If the patient is outside a facility, then the patient management system 46 also, optionally, provides the caretaker(s) 102 with information on the nearest facility where the patient can be taken, and alert the staff at the facility as to the condition of the patient, and the alert condition which was generated.

The system 10 brings together expertise in biomaterials, sensors, electronics, real-time monitoring, time-series analysis, cloud based analytics, stroke and emergency neurology, to provide a commercially attractive real-time monitoring system for rapid transmission of acute stroke systems. These efforts rapidly set the stage for use in patients, wireless communication of potential stroke syndromes in real-time, and activation of acute stroke protocols. The system has been described, in part for application for ischemic stroke, but it can be appreciated that it is equally applicable for both ischemic and hemorrhagic stroke. The result is a product ready for immediate use where there is a clear and urgent need to improve the delivery of care for patients with stroke.

The system is also applicable for the detection and quantification of focal deficits which result from acute central nervous system injury or injury in general. It is appreciated that the measurements and analysis described allow quantification of focal deficits due to injury, and provide a quantitative marker for both normal function and the loss of function due to injury. Such quantification is invaluable for rehabilitation. This quantification may be more broadly applied as well. It is also contemplated the present system 10 may be applied as a surrogate measure for overall well-being by quantifying normal levels of activity for an individual and detecting changes from these levels. For example, it is contemplated the present system 10 may be applied in conjunction with the treatment and detection of neurological and psychiatric illnesses such as psychoses, depression, post-traumatic stress-disorder, muscular sclerosis, and Parkinsonism.

The system 10 may also be used to quantify the neurological exam. Here, an individual is asked to sit, stand and perform stereotyped movements, and the system 10 documents and quantifies the limb activity, and compares them against a normative database to allow a quantitative comparison to a normal population. This examination can be performed at a remote location, facilitating telemedicine. In a second extension, the system 10 is embedded within a game which can be played on smartphones and on gaming devices. This allows the quantitative determination of limb activity while an individual is playing a game, and the detection of subtle movement disorder through game playing.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method comprising:
receiving, at an acquisition system, sensor measurements data from a plurality of body worn sensors including a first sensor for periodically measuring real-time natural limb activity for a left limb of a patient and a second sensor for periodically measuring real-time, natural limb activity for a right limb of a patient;
periodically processing, at a data processing system, sensor measurements data received from the acquisition system to determine a first patient specific limb activity signature for a left limb of the patient and a second patient specific limb activity signature for a right limb of the patient based on periodically sampled data acquired over a first period of time; and
detecting an anomaly in limb activity of the patient by comparing sensor measurements data received from the acquisition system based on periodically sampled data acquired over a second period of time with the first patient specific limb activity signature and/or the second patient specific limb activity signature.

2. The method according to claim 1, wherein the plurality of body worn sensors includes four body worn sensors shaped and dimensioned to be worn on limbs of the patient and wherein the sensor measurements data from each of the plurality of body worn sensors is relayed to a patient worn data transmission device for transmitting the sensor measurements data from the patient worn data transmission device to the acquisition system.

3. The method according to claim 1, further comprising adding a time-stamp, using the data processing system, to data conveyed by a patient worn data transmission device.

4. The method according to claim 1, wherein at least one of the plurality of body worn sensors includes a motion tracking device.

5. The method according to claim 1, wherein the step of conveying the measurements includes adding a time-stamp to a data stream generated by at least one of the plurality of body worn sensors.

6. The method according to claim 1, further comprising identifying treatment protocols using the data processing system.

7. The method according to claim 6, further comprising generating an alert in response to detecting the anomaly in limb activity of the patient, wherein the treatment protocols include activation of an emergency medical response system and transport of the patient to a nearest Neurocritical Care Unit or emergency room for rapid evaluation and treatment.

8. The method according to claim 1, further comprising:
creating a first diffusion map based on the processed sensor measurements data received from the acquisition system to generate the first patient specific limb activity signature for the left limb of the patient based on the periodically sampled data acquired over the first period of time, wherein the first diffusion map is a multi-dimensional representation of the left limb activity of the patient;
creating a second diffusion map based on the processed sensor measurements data received from the acquisition system to generate the second patient specific limb activity signature for the right limb of the patient based on the periodically sampled data acquired over the first period of time, wherein the second diffusion map is a multi-dimensional representation of the right limb activity of the patient;
creating a third diffusion map based on the processed sensor measurements data received from the acquisition system to generate a third patient limb activity signature for both the left and right limbs of the patient based on the periodically sampled data acquired over the first period of time, wherein the third diffusion map is a multi-dimensional representation of the activity of both the left and right limb activity of the patient; and
detecting the anomaly in limb activity of the patient if the limb activity of the patient based on periodically sampled data acquired over a later period of time deviates from the first patient specific limb activity signature, the second patient specific limb activity signature, and/or the third patient specific limb activity signature by a pre-established extent.

9. The method according to claim 1, further comprising periodically updating the first patient specific limb activity signature for the left limb of the patient and the second patient specific limb activity signature for the right limb of the patient based on periodically sampled data acquired over a later period of time.

10. The method according to claim 1, further comprising:
generating an asymmetry signature for the patient based on periodically sampled data acquired over the first period of time wherein the asymmetry signature quantifies a magnitude of a deficit in limb activity for the left limb of the patient relative to the right limb of the patient; and
detecting an anomalous asymmetry in limb activity of the patient by comparing sensor measurements data received from the acquisition system based on periodically sampled data acquired over a second period of time with the asymmetry signature for the patient.

11. The method according to claim 1, further comprising:
periodically updating the first patient specific limb activity signature for the left limb of the patient and the second patient specific limb activity signature for the right limb of the patient based on periodically sampled data acquired over a later period of time; and
detect a deficit in limb activity for the left limb of the patient or the right limb of the patient by comparing sensor measurements data received from the acquisition system based on periodically sampled data acquired over the second period of time using the first patient specific limb activity signature for the left limb of the patient or the second patient specific limb activity signature for the right limb of the patient, respectively.

12. The method according to claim 1, further comprising:
tracking an ensemble of diffusion geometry measurements and time-series measures of signal magnitude, variability, complexity and interrelation determined from the sensor measurements data of the plurality of body worn sensors.

13. A system compromising:
an acquisition system that receives sensor measurements data from a plurality of body worn sensors including a first sensor for periodically measuring real-time natural limb activity for a left limb of a patient and a second sensor for periodically measuring real-time natural limb activity for a right limb of a patient; and
a data processing system that includes an analysis system that includes a processor that is configured to:

periodically process the sensor measurements data received from the acquisition system to determine a first patient specific limb activity signature for a left limb of the patient and a second patient specific limb activity signature for a right limb of the patient based on periodically sampled data acquired over a first period of time; and detect an anomaly in limb activity of the patient by comparing sensor measurements data received from the acquisition system based on periodically sampled data acquired over a second period of time with the first patient specific limb activity signature and/or the second patient specific limb activity signature.

14. The system according to claim 13, wherein the plurality of body worn sensors includes four body worn sensors shaped and dimensioned to be worn on limbs of the patient, and wherein the sensor measurements data from each of the plurality of body worn sensors is relayed to a patient worn data transmission device for transmitting the sensor measurements data from the patient worn data transmission device to the acquisition system.

15. The system according to claim 13, wherein the plurality of body worn sensors includes four body worn sensors shaped and dimensioned to be worn on limbs of the patient, and wherein the sensor measurements data from each of the plurality of body worn sensors is relayed to a patient worn data transmission device for transmitting the sensor measurements data from the patient worn data transmission device to the acquisition system.

16. The system according to claim 13, wherein the patient worn data transmissions device adds a time-stamp to a data stream generated at least one of the plurality of body worn sensors.

17. The system according to claim 13, wherein the data processing system adds a time-stamp to data conveyed by a patient worn data transmission device.

18. The system according to claim 13, wherein at least one of the plurality of body worn sensors includes a motion tracking device.

19. The system according to claim 13, wherein the data processing system identifies treatment protocols.

20. The system according to claim 19, wherein the system generates an alert in response to detecting the anomaly in limb activity of the patient, and wherein the treatment protocols include activation of an emergency medical response system and transport of the patient to a nearest Neurocritical Care Unit or emergency room for rapid evaluation and treatment.

21. The system according to claim 13, wherein the processor is further configured to:

create a first diffusion map based on the processed sensor measurements data received from the acquisition system to generate the first patient specific limb activity signature for the left limb of the patient based on the periodically sampled data acquired over the first period of time, wherein the first diffusion map is a multi-dimensional representation of the left limb activity of the patient;

create a second diffusion map based on the processed sensor measurements data received from the acquisition system to generate the second patient specific limb activity signature for the right limb of the patient based on the periodically sampled data acquired over the first period of time, wherein the second diffusion map is a multi-dimensional representation of the right limb activity of the patient;

create a third diffusion map based on the processed sensor measurements data received from the acquisition system to generate a third patient limb activity signature for both the left and right limbs of the patient based on the periodically sampled data acquired over the first period of time, wherein the third diffusion map is a multi-dimensional representation of the activity of both the left and right limb activity of the patient; and detect the anomaly in limb activity of the patient if the limb activity of the patient based on periodically sampled data acquired over a later period of time deviates from the first patient specific limb activity signature the second patient specific limb activity signature, and/or the third patient specific limb activity signature by a pre-established extent.

22. The system according to claim 13, wherein the processor is further configured to:

periodically update the first patient specific limb activity signature for the left limb of the patient and the second patient specific limb activity signature for the right limb of the patient based on periodically sampled data acquired over a later period of time.

23. The system according to claim 13, wherein the processor is further configured to:

generate an asymmetry signature for the patient based on periodically sampled data acquired over the first period of time wherein the asymmetry signature quantifies a magnitude of a deficit in limb activity for the left limb of the patient relative to the right limb of the patient; and detect an anomalous asymmetry in limb activity of the patient by comparing sensor measurements data received from the acquisition system based on periodically sampled data acquired over a second period of time with the asymmetry signature for the patient.

24. The system according to claim 13, wherein the processor is further configured to:

periodically update the first patient specific limb activity signature for the left limb of the patient and the second patient specific limb activity signature for the right limb of the patient based on periodically sampled data acquired over a later period of time; and detect a deficit in limb activity for the left limb of the patient or the right limb of the patient by comparing sensor measurements data received from the acquisition system based on periodically sampled data acquired over the second period of time using the first patient specific limb activity signature for the left limb of the patient or the second patient specific limb activity signature for the right limb of the patient, respectively.

25. The system according to claim 13, wherein the processor is further configured to:

track an ensemble of diffusion geometry measurements and time-series measures of signal magnitude, variability, complexity and interrelation determined from the sensor measurements data of the plurality of body worn sensors.

* * * * *